United States Patent [19]

Uchikuga et al.

[11] 4,250,109

[45] Feb. 10, 1981

[54] PROCESS FOR PREPARING HEXAMETHYLENE BIS-DICYANDIAMIDE

[75] Inventors: Saburo Uchikuga, Yokohama; Michiro Itoh, Hachioji; Katsuyasu Nagahama, Sagamihara, all of Japan

[73] Assignee: Sogo Pharmaceutical Company Limited, Kanagawa, Japan

[21] Appl. No.: 65,144

[22] Filed: Aug. 7, 1979

[30] Foreign Application Priority Data

Aug. 31, 1978 [JP] Japan ................................. 53-105490

[51] Int. Cl.³ .......................................... C07C 145/04
[52] U.S. Cl. .................................................... 564/104
[58] Field of Search .................................... 260/551 C

[56] References Cited

U.S. PATENT DOCUMENTS

| 2,697,727 | 12/1954 | Kaiser et al. | 260/551 C |
| 3,597,466 | 8/1971 | Smith | 260/551 C |
| 4,157,340 | 6/1979 | Crenshaw et al. | 260/551 C |
| 4,158,013 | 6/1979 | Crenshaw et al. | 260/551 C |
| 4,163,056 | 7/1979 | Kristiansen et al. | 260/551 C |

OTHER PUBLICATIONS

*Journal of Organic Chemistry,* vol. 32 pp. 1566–1572, Timmons et al., "The Chemisty of Cyanodithioimidocarbonic Acid," 1966.

*Primary Examiner*—Winston A. Douglas
*Assistant Examiner*—Raymond K. Covington
*Attorney, Agent, or Firm*—Browdy and Neimark

[57] ABSTRACT

Hexamethylene.bis-dicyandiamide is safely prepared in good yield and desired purity by a novel method which comprises reacting N-cyano-O (or S)-alkyl-iso (or isothio) urea with hexamethylenediamine. The desired product is useful as an intermediate of chlorhexidine which is an antibacterial agent.

2 Claims, No Drawings

PROCESS FOR PREPARING HEXAMETHYLENE BIS-DICYANDIAMIDE

This invention relates to a novel method for preparing hexamethylene.bis-dicyandiamide in good yield and desired purity without using any poisonous substances.

Hexamethylene.bis-dicyandiamide having the following formula (V):

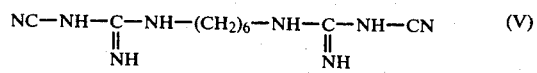

is useful as an intermediate or starting material for 1:6-di ($N^5$-p-chlorophenyl-$N^1$-diguanide) hexane (general name: chlorhexidine) which is a strongly effective antibacterial-antiseptic agent against both Gram-positive and Gram-negative bacteria and has the following formula (VI):

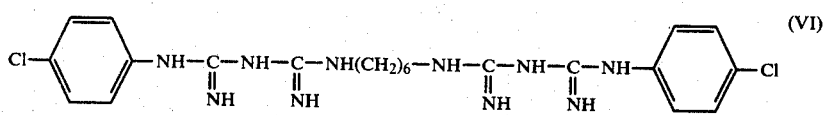

At present, hexamethylene.bis-dicyandiamide (V) is produced by reacting dicyanimide.alkali salt with hexamethylenediamine.dihydrochloride; however, since dicyanimide.alkali salt which is the starting material is produced by reacting cyanamide such as sodium cyanamide with cyanogen halide such as cyanogen bromide, there are large drawbacks as follows:

That is to say, first of all, because cyanogen halide is virulently poisonous it is very difficult to handle and very dangerous; therefore, it is extremely difficult to obtain dicyanimide.alkali salt. In the second place, at the time of reaction of cyanamide.alkali salt with cyanogen halide, in addition to dicyanimide.alkali salt, alkali halide is produced by side reaction but this by-product is extremely difficult to remove. Namely, it is very difficult to produce dicyanimide.alkali salt which does not contain alkali halide; in other words, it is very difficult to obtain dicyanimide.alkali salt of high purity. Therefore, in the third place, the yield of hexamethylene.bis-dicyandiamide (V) decreases due to low purity of dicyanimide.alkali salt, resulting in decrease of yield of chlorhexidine.

The present invention has been completed in order to overcome such drawbacks as lack of safety, difficulty of of producing the starting material and decrease of yield.

First of all, being essentially different from the prior art method, the significant characteristic of the present invention lies in that, as the starting material, the following compound (I), (II) or (III) is used for the first time instead of dicyanimide.alkali salt which has numerous drawbacks described above. The compound (I), (II) or (III), having the following formulas, respectively, can be easily obtained and is a compound of high safety:

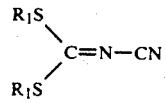 (I)

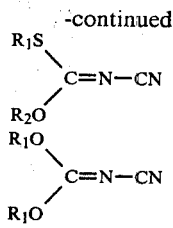

(wherein $R_1$ and $R_2$ are alkyl groups of one to ten carbon atoms.)

Next, according to the present invention, the compound (I), (II) or (III) is reacted with ammonia, ammonium carbonate or ammonium bicarbonate, then with hexamethylenediamine. At this time a novel reaction mechanism has been discovered, and therefore the significant characteristic of the present invention also lies in that the present invention has been completed on the basis of this discovery of the novel reaction mechanism as follows:

Namely, it has been found that there is extremely high selectivity, such that ammonia and (free) hexamethylenediamine are reacted with only the S (or O)-alkyl group of the compound (I), (II) or (III); however, they are never reacted with the cyano group, and furthermore, simultaneously it has also been found that the high selectivity above described can be obtained only by ammonia, ammonium carbonate or ammonium bicarbonate and hexamethylenediamine.

Therefore, the significant characteristic of the present invention lies in novel development of the specific starting materials and novel process wherein ammonia, ammonium carbonate or ammonium bicarbonate and hexamethylenediamine are allowed to react.

Dialkyl-ester of cyanamidedithiocarbonic acid (I), which is one of the starting materials, can be easily obtained from dialkali salt of cyanodithiocarbonic acid, and O-alkyl-S-alkyl-ester of cyanamidethiocarbonic acid (II) can be easily obtained from xanthates.

Also, dialkyl-ester of N-cyanoimidocarbonic acid (III) can be relatively easily obtained [Chem. Ber. 100 2604 (1967)], so that these starting materials are very available compounds and also they are very safe compounds without any dangerousness.

In relating to the reaction temperature according to the method of this invention, in the case of the reaction wherein the compound (I), (II) or (III) is reacted with ammonia ($NH_4OH$) or carbonate thereof ($(NH_4)_2CO_3$ or $(NH_4)HCO_3$ to yield N-cyano-O (or S)-alkyl-iso (or isothio) urea having the following formula (IV):

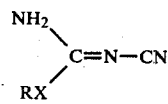

(wherein R is an alkyl group of one to ten carbon atoms and X is an oxygen or sulfur atom), the reaction temperature is from 0° C. to 50° C. and preferably room temperature. In the case of the subsequent reaction with hexamethylenediamine to yield hexamethylene.bis-dicyandiamide (V), the reaction temperature may vary within the range from room temperature to 170° C., the preferred range being from 50° C. to 130° C. The reaction duration is respectively varied according to each reaction stage, the suitable range being from 1 to 24 hours. As a reaction medium, various media may be widely used and among them water and alcohol are preferable.

Next, the present invention is described in the following Example and, moreover, in the Referential Example relating to the method of producing mineral acid salts of chlorhexidine (VI) by reacting hexamethylene.bis-dicyandiamide (V) produced according to the present invention with mineral acid salts of p-chloroaniline.

It should be noted that, although the reaction of hexamethylene.bis-dicyandiamide (V) with mineral acid salts of p-chloraniline (generally, hydrochloride) is effected by conventional techniques, the mineral acid salts of chlorhexidine are prepared for the first time in excellent yield and good purity since, according to the present invention, the production of hexamethylene.bis-dicyandiamide (V) is extremely superior to the prior art methods in safety, ease of production and purity as described above. The mineral acid salts may be converted to the free chlorhexidine by treating with alkali and then, generally, reconverted to water soluble chlorhexidine.digluconate which can be used as the antibacterial-antiseptic agent.

EXAMPLE 1

(i) A solution of 28.8 g of O-ethyl-S-methylester of cyanamidethiocarbonic acid in 34 ml of methanol is added dropwise with 20 ml of concentrated aqueous ammonia with cooling by ice, and then the reaction is carried out with stirring at 10° C. and below for 1 hour subsequently at room temperature for 24 hours. Next, the solvent is removed under reduced pressure, and the residue is added with 20 ml of water to give crystal which is filtered off then dried to yield 19.6 g of cyano-O-ethylisourea, m.p. 118°–119° C. (yield 86.6%).

(ii) 19.6 g of cyano-O-ethylisourea and 10.1 g of hexamethylenediamine are dissolved in 33 ml of water and the reaction is carried out at 105° C. for 20 hours in a sealed ampul. Next, the solvent is evaporated to dryness under reduced pressure, and the residue is added with 65 ml of water. The thus formed mixture is dispersed with warming, subsequently cooled and filtered off to yield crystal. At this time, the crystal is washed with cooled alcohol. Thus obtained crystal is dried to yield 19.1 g of hexamethylene.bis-dicyandiamide, m.p. 202°–203° C. (yield 88.2%).

EXAMPLE 2

Employing the procedure outlined in Example 1 (i), the following esters of cyanamidethiocarbonic acid are employed as a starting material in place of O-ethyl-S-methyl ester of cyanamidethiocarbonic acid to yield respectively the corresponding cyano-O-alkylisoureas in good yield of 87.0 to 98.0%: O-methyl-S-methyl ester; O-isopropyl-S-methyl ester; O-n-butyl-S-methyl ester; O-n-amyl-S-methyl ester; and O-n-octyl-S-methyl ester of cyanamidethiocarbonic acid.

Similarly as in Example 1 (ii), hexamethylenediamine is reacted therewith to yield respectively hexamethylene.bis-dicyandiamide in the following yields (m.p. 202°–203° C.):

| Cyano-O-alkyl isourea | Process temperature (°C.) | Process duration (hour) | Yield of hexamethylene bis-dicyandiamide (%) |
|---|---|---|---|
| Cyano-O-methyl isourea | 105.0 | 15.0 | 33.6 |
| Cyano-O-isopropyl isourea | 75.0 | 2.0 | 71.3 |
| Cyano-O-n-butyl isourea | 60.0 | 1.0 | 75.4 |
| Cyano-O-n-amyl isourea | 80.0 | 2.0 | 43.6 |
| Cyano-O-n-octyl isourea | 80.0 | 2.0 | 63.0 |

EXAMPLE 3

(i) A solution of 7.9 g of O-ethyl-S-ethyl-ester of cyanamidethiocarbonic acid in 30 ml of methanol is added dropwise with 10 ml of concentrated aqueous ammonia with cooling by ice, and then the reaction is effected with stirring at room temperature for 20 hours. Next, the solvent is removed under reduced pressure, and the residue is added with 10 ml of water, thus formed crystal is filtered off then dried to yield 4.9 g of cyano-O-ethylisourea, m.p. 118°–119° C. (yield 87.3%).

(ii) Similarly as in Example 1(ii), the reaction is effected to yield hexamethylene.bis-dicyandiamide, m.p. 202°–203° C. (yield 87.8%).

EXAMPLE 4

(i) A solution of 30.5 g of dimethyl-ester of cyanamidedithiocarbonic acid (m.p. 49°–51° C.) in 36 ml of methanol is added dropwise with 21 ml of concentrated aqueous ammonia with cooling by ice, and then the reaction is carried out with stirring at 10° C. and below for 1 hour and subsequently at room temperature for 24 hours. Next, the solvent is removed under reduced pressure, and the residue is added with 20 ml of water to give crystal which is filtered and then dried to yield 21.8 g of cyano-S-methylisothiourea (yield 90.7%).

(ii) 21.8 g of cyano-S-methylisothiourea and 11.0 g of hexamethylenediamine are dissolved in 60 ml of water and the reaction is carried out at 105° C. for 20 hours in a sealed ampul. Next, the solvent is evaporated to dryness under reduced pressure, and the residue is added with 70 ml of water. The thus formed mixture is then dispersed with warming, subsequently cooled and filtered to yield crystal. At this time, the crystal is washed with cooled alcohol. Thus obtained crystal is dried to yield 21.3 g of hexamethylene.bis-dicyandiamide, m.p. 202°–203° C. (yield 89.9%).

EXAMPLE 5

(i) A solution of 23.5 g of diethyl-ester of cyanamidedithiocarbonic acid in 33 ml of methanol is added dropwise with 15 ml of concentrated aqueous ammonia with cooling by ice, and then the reaction is carried out with stirring at room temperature for 24 hours. Next, the solvent is removed under reduced pressure, and the residue is added with 15 ml of water to give crystal which is filtered and dried to yield 17.8 g of cyano-S-ethylisothiourea (yield 94.7%).

(ii) 17.8 g of cyano-S-ethylisothiourea and 7.6 g of hexamethylenediamine are dissolved in 80 ml of water and the reaction is carried out at 105° C. for 17 hours in a sealed ampul. Next, the solvent is evaporated to dryness under reduced pressure, and the residue is added with 50 ml of water. The thus formed mixture is then dispersed with warming, subsequently cooled and filtered to yield crystal. At this time, the crystal is washed with cooled alcohol. Thus obtained crystal is dried to yield 13.3 g of hexamethylene.bis-dicyandiamide, m.p. 202°–203° C. (yield 81.6%).

EXAMPLE 6

(i) A solution of 14.2 g of diethyl-ester of N-cyano-imidocarbonic acid in 20 ml of methanol is added dropwise with 10 ml of concentrated aqueous ammonia with cooling by ice, and then the reaction is carried out with stirring at room temperature for 18 hours. Next, the solvent is evaporated under reduced pressure, and the residue is added with 10 ml of water to give crystal which is filtered and dried to yield 10.3 g of cyano-O-ethylisourea (yield 91.2%).

(ii) Similarly as in Example 1 (ii), the reaction is effected to yield hexamethylene.bis-dicyandiamide, m.p. 202°–203° C. (yield 88.6%).

EXAMPLE 7

Using dimethyl-ester of N-cyano-imidocarbonic acid obtained by the method such as described in Chem. Ber. 100 2604 (1967), the procedure described in Example 6 is repeated to yield hexamethylene.bis-dicyandiamide.

Referential Example 1

19.1 g of hexamethylene.bis-dicyandiamide obtained in Example 1 (i)(ii) and 25.0 g of p-chloroaniline hydrochloride are dissolved in 180 ml of 2-ethoxyethanol with warming, then the mixture is refluxed for 3 hours with stirring. Next, the reaction mixture is cooled and crystal is filtered and dried to yield 39.7 g of chlorhexidine hydrochloride, m.p. 260°–262° C. (yield 90.3%).

I.R. and m.p. thereof are identical with those of specimen.

Referential Example 2

In the same manner as in Referential Example 1, hexamethylene.bis-dicyandiamide obtained in Example 2 is reacted with p-chloroaniline hydrochloride to yield chlorhexidine hydrochloride, m.p. 260°–262° C. (yield 89.6%).

I.R. and m.p. thereof are identical with those of specimen.

Referential Example 3

Using hexamethylene.bis-dicyandiamide obtained in Example 3 (i)(ii) and employing the procedure outlined in Referential Example 1, the reaction is carried out to yield chlorhexidine hydrochloride, m.p. 260°–262° C. (yield 89.3%).

I.R. and m.p. thereof conforms to those of specimen.

Referential Example 4

21.3 g of hexamethylene.bis-dicyandiamide obtained in Example 4 (i)(ii) and 27.9 g of p-chloroaniline hydrochloride are dissolved in 200 ml of 2-ethoxyethanol with warming, then the mixture is refluxed for 3 hours with stirring. Next, the reaction mixture is cooled and crystal is filtered and dried to yield 40.4 g of chlorhexidine hydrochloride, m.p. 260°–262° C. (yield 82.1%).

I.R. and m.p. thereof are identical with those of specimen.

Referential Example 5

Using hexamethylene.bis-dicyandiamide obtained in Example 5 (i)(ii) and employing the procedure outlined in Referential Example 1, the reaction is carried out to yield chlorhexidine hydrochloride, m.p. 260°–262° C. (yield 85.4%).

I.R. and m.p. thereof conforms to those of referential standards.

Referential Example 6

Using hexamethylene.bis-dicyandiamide obtained in Example 6 (i)(ii) and employing the procedure outlined in Referential Example 1, the reaction is carried out to yield chlorhexidine hydrochloride, m.p. 260°–262° C. (yield 87.5%).

Referential Example 7

In the same manner as in Referential Example 1, hexamethylene.bis-dicyandiamide (V) obtained in Example 7 is reacted to yield chlorhexidine hydrochloride (m.p. 260°–262° C.).

What is claimed is:

1. A process for preparing hexamethylene.bis-dicyandiamide of the following formula:

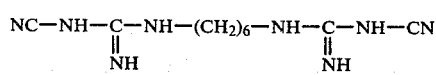

characterized in that the process comprises reacting a compound of the following formula:

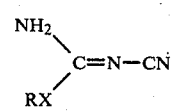

wherein R is an alkyl group of one to ten carbon atoms and X is an oxygen or sulfur atom,
with hexamethylenediamine.

2. A process for preparing hexamethylene.bis-dicyandiamide of the following formula:

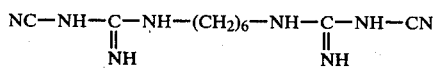

characterized in that the process comprises reacting a starting material selected from the group consisting of compounds having the following formulae:

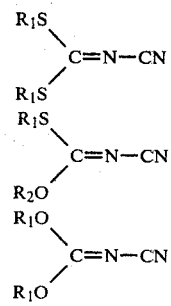

wherein $R_1$ and $R_2$ are alkyl groups of one to ten carbon atoms, with ammonia, ammonium carbonate or ammonium bicarbonate to yield a compound of the following formula:
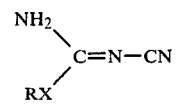
wherein R is an alkyl group of one to ten carbon atoms and X is an oxygen or sulfur atom,
which is then reacted with hexamethylenediamine.
* * * * *